United States Patent [19]

Winkley et al.

[11] 4,438,031

[45] Mar. 20, 1984

[54] N-(ALKYLSULFONYL)-L-PROLINE AMIDE AND N-(ALKYLSULFONYL)-2-CARBOXYLIC ACID AMIDE-INDOLINE DERIVATIVES

[75] Inventors: Michael W. Winkley, Malvern; Scott J. Childress, Philadelphia, both of Pa.

[73] Assignee: American Home Products Corporation, New York, N.Y.

[21] Appl. No.: 351,716

[22] Filed: Feb. 24, 1982

[51] Int. Cl.³ ............... C07D 209/26; C07D 207/16; C07D 277/06; C07C 103/52
[52] U.S. Cl. .................. 260/112.5 R; 260/238 A; 548/200; 548/493; 548/538; 544/54; 546/245
[58] Field of Search .............. 548/200, 538, 493; 260/112.5 R, 239 A; 544/54; 546/245

[56] References Cited

U.S. PATENT DOCUMENTS

| | | | |
|---|---|---|---|
| 4,046,889 | 9/1977 | Ondetti et al. | 424/244 |
| 4,105,776 | 8/1978 | Ondetti et al. | 424/274 |
| 4,237,134 | 12/1980 | Ondetti | 424/248.52 |
| 4,284,561 | 8/1981 | Petrillo et al. | 260/326.2 |
| 4,303,583 | 12/1981 | Kim et al. | 260/239.3 T |
| 4,396,773 | 8/1983 | Kim et al. | 548/491 |

FOREIGN PATENT DOCUMENTS

| | | |
|---|---|---|
| 872972 | 6/1979 | Belgium . |
| 868532 | 10/1979 | Belgium . |
| 12401 | 6/1980 | European Pat. Off. . |
| 2934592 | 3/1980 | Fed. Rep. of Germany . |
| 2937779 | 4/1981 | Fed. Rep. of Germany . |
| 2027025 | 2/1980 | United Kingdom . |

OTHER PUBLICATIONS

Derwent Abstract No. 22968 C/13 of Japanese Kokai No. 55022-673, Published 2/18/80.
Derwent Abstract No. 15734 C/09 of Japanese Kokai No. 550009-060, Published 1/22/80.

*Primary Examiner*—Robert Gerstl
*Attorney, Agent, or Firm*—Arthur G. Seifert

[57] ABSTRACT

Disclosed herein are (lower)alkylsulfonyl derivatives of various proline amides, thiazolidine carboxylic acid amides and indoline-2-carboxylic acid amides, among others, which inhibit angiotensin converting enzyme and are antihypertensive agents.

23 Claims, No Drawings

N-(ALKYLSULFONYL)-L-PROLINE AMIDE AND N-(ALKYLSULFONYL)-2-CARBOXYLIC ACID AMIDE-INDOLINE DERIVATIVES

This invention concerns (lower)alkylsulfonylamides of proline and indoline-2-carboxylic acid which act as inhibitors of angiotensin converting enzyme and as anti-hypertensive agents.

The compounds of the invention have the general formula:

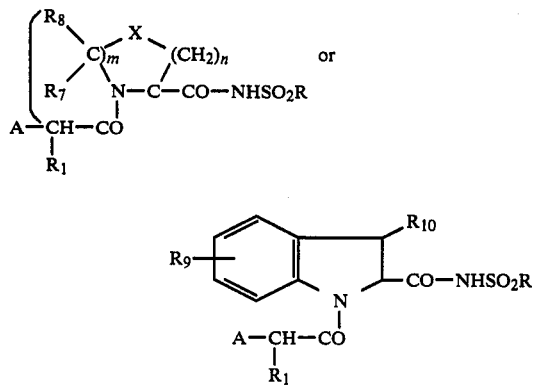

wherein:
m is 0 or 1, and m is 1 when X is S;
n is 1 or 2;
X is —$CH_2$— or S;
R is methyl, ethyl, n-propyl, or iso-propyl;
$R_7$ is hydrogen, lower alkyl, lower alkoxy, phenyl, or substituted phenyl;
$R_8$ is hydrogen or lower alkyl;
$R_9$ is hydrogen, hydroxy, lower alkyl, lower alkoxy, or halogen;
$R_{10}$ is hydrogen or lower alkyl;
$R_1$ is hydrogen, lower alkyl, phenyl, substituted phenyl, phen lower alkyl, substituted phen lower alkyl, amino lower alkyl, or perfluoroalkyl;
A is:

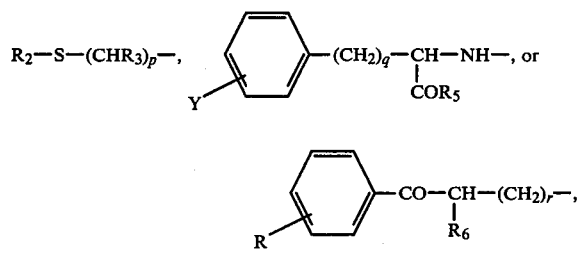

in which:
$R_2$ is hydrogen or $R_4CO$— where $R_4$ is hydrogen, lower alkyl, phenyl, substituted phenyl, phen lower alkyl, or substituted phen lower alkyl;
$R_3$ is hydrogen, lower alkyl, benzoyl, or substituted benzoyl;
$R_6$ is $SR_{11}$ where $R_{11}$ is hydrogen, lower alkanoyl, benzoyl, substituted benzoyl, benzoxycarbonyl, or substituted benzoxycarbonyl;
$R_5$ is hydroxy, lower alkoxy or amino;
Y is a halogen, a lower alkyl group, or a lower alkoxy group, or hydrogen;
p is 0 or 1;
q is 0–3; and
r is 0 or 1.

In the above formula and elsewhere in this specification and claims, the following definitions apply: "lower alkyl" refers to saturated hydrocarbon groups having 1–6 carbon atoms; "lower alkoxy" refers to (saturated) alkoxy groups having 1–6 carbon atoms; "substituted phenyl", "substituted phen lower alkyl", "substituted benzoyl", and "substituted benzoxycarbonyl" each refer to such a group having a halogen, a lower alkyl group, or a lower alkoxy group on the phenyl ring thereof; "phen lower alkyl" refers to a phenyl group attached to a saturated hydrocarbon group of 1–6 carbon atoms; "amino lower alkyl" refers to an amino group (unsubstituted) attached to a saturated hydrocarbon group of 1–6 carbon atoms; "perfluoralkyl" refers to —$CF_3$ or $CF_3CF_2$—; "lower alkanoyl" refers to a carbonyl group attached to a saturated hydrocarbon group of 1–6 carbon atoms; and "halogen" refers to fluorine, chlorine and bromine. In general, for a lower alkyl group and groups having a saturated hydrocarbon group as a part thereof, a saturated hydrocarbon group of 1–3 carbon atoms is preferred.

BACKGROUND OF THE INVENTION

In pharmacological research on hypertension, recent attention has focused on the study of the renin-angiotensin-aldosterone system, and, in particular, on the development of an effective anti-hypertensive agent which would, theoretically, achieve its result by inhibiting the action of angiotensin converting enzyme in converting angiotensin I to angiotensin II. The inhibition of the production of angiotensin II became important because of the discoveries that angiotensin II is the most potent pressor agent (vasoconstrictor) present in the mammalian body and, in addition, stimulates the adrenal cortex to release aldosterone, thereby causing excessive sodium retention and fluid retention, contributing further to the hypertensive state. Thus, inhibiting the conversion of angiotensin I to angiotensin II is believed to work directly on the primary biochemical mechanisms creating increased blood pressure. For a description of the mechanisms and of the mammalian renal-angiotensin-aldosterone system, see Hypertension, Genest et al., ed., Chapters 6.2 and 7.3 (McGraw-Hill, 1977) and John H. Laragh, "The Renin System in High Blood Pressure, From Disbelief to Reality: Converting-Enzyme Blockade for Analysis and Treatment", Prog. in Cardio. Vasc. Disease, XXI, No. 3, 159–166 (November, 1978).

As described by Suzanne Oparil in Genest et al., supra, Chapter 6.3, two of the most potent and most studied inhibitors of angiotensin converting enzyme are the Bothrops jararaca snake venom extracts, the pentapeptide (Pyr-Lys-Trp-Ala-Pro), also referred to as $BPP_{5a}$, and the nonapeptide (Pyr-Trp-Pro-Arg-Pro-Gln-Ile-Pro-Pro), also referred to as $BPP_{9a}$. (BPP stands for Bradykinin Potentiating Peptide). $BPP_{9a}$ has been shown to be an effective anti-hypertensive agent in clinical studies on humans with certain forms of hypertension. However, $BPP_{9a}$ is not orally active as an anti-hypertensive agent. For a summary of the clinical aspects of $BPP_{9a}$ see Genest et al., supra, Chapter 6.3, pp. 163–4.

Such studies led to the development of a series of proline derivatives which were significantly more potent as inhibitors of angiotensin converting enzyme and as anti-hypertensive agents than $BPP_{9a}$. Of these proline derivatives, D-3-mercapto-2-methylpropanoyl-L-proline has been reported to be the most effective, including being effective when administered orally. These proline and mercaptoproline derivatives and various pharmacological test results thereon are described in Cushman et al., "Design of New Anti-hypertensive Drugs: Potent and Specific Inhibitors of Angiotensin Converting Enzyme", Prog. in Cardio. Diseases, Vol. XXI, No. 3 (Nov./Dec., 1978), and in U.S. Pat. Nos. 4,046,889 (a) and 4,105,776 (b), both to Ondetti and Cushman.

Subsequently, other proline derivatives and various pipecolic acid and thiazolidinecarboxylic acid derivatives were also disclosed as having angiotensin converting enzyme (ACE) inhibition and anti-hypertensive properties in the following publications:

(c) U.S. Pat. No. 4,237,134, dated Dec. 2, 1980, to Ondetti;

(d) Belgium Brevet D'Invention No. 868,532, published Oct. 16, 1978, to Yoshitomi Pharmaceutical Industries, Ltd. (also United Kingdom Patent Specification No. 2,000,508);

(e) Derwent Abstract No. 22968 C/13 of Japanese Kokai No. 55022-673, published Feb. 18, 1980, to Yoshimoto Pharmaceutical Industries, Ltd.;

(f) Derwent Abstract No. 15734 C/09 of Japanese Kokai No. 550009-060, published Jan. 22, 1980, to Yoshimoto Pharmaceutical Industries, Ltd.;

(g) German Offenlegungsschrift No. 29 34 592, published Mar. 20, 1980, to American Cyanamid Co.;

(h) European Patent Publication No. 0012401, published June 6, 1980, to Merck & Co.; and (i) Belgium Brevet D'Invention No. 872,972, published June 21, 1979, to Science Union et cie, Societe Francaise de Recherche Medicale.

Further, indoline and quinoline carboxylic acid derivatives having angiotensin converting enzyme inhibition and antihypertensive properties are described in the following:

(j) German Offenlegungsschrift No. 29 37 779, published Apr. 9, 1981, to Hoechst AG;

(k) U.S. Pat. No. 4,303,583, issued Dec. 1, 1981, to D. H. Kim et al.;

(l) U.K. Patent Application No. 2,027,025, published Feb. 13, 1980, to Santen Pharmaceutical Co., Ltd., and (m) U.S. Pat. No. 4,284,561, issued Aug. 18, 1981, to Petrillo et al.

These references disclose pyridines, thiazolidines, and indolines, among others, substituted at the 2 position with carboxylic acids or esters and amides. EPC Pub. No. 0012401 (g) and Belgium Brevet D'Invention No. 872,972 (h), above, additionally disclose amides at the 2 position which are substituted on the amino group thereof by one or two alkyl groups, an hydroxy group, or a benzyl group, or the 2-carbonyl group is substituted with an "acylamino alkoxy" group. U.S. Pat. No. 4,284,561 (m) also discloses hydroxamic acids. Such substituents are unrelated to the alkylsulfonylamino substituents of the present invention.

DETAILED DESCRIPTION OF THE INVENTION

Preferred compounds of Formula Ia are those in which X is —CH$_2$— and m and n are both 1. Preferred compounds of Formula Ia in which X is S are those wherein m and n are both 1. Preferred R$_7$ substituents are hydrogen and phenyl, and the preferred R$_8$ substituent is hydrogen. The preferred R$_9$ and R$_{10}$ substituent of Formula Ib is hydrogen.

Where A is R$_2$—S—(CHR$_3$)$_p$— in either Formula Ia or Ib, preferred substituents are, independently, p is 1; R$_3$ is hydrogen or benzoyl; and R$_2$ is hydrogen, benzoyl or acetyl. Particularly preferred are such A substituents wherein R$_2$ is hydrogen, p is 1, and R$_3$ is hydrogen. The latter are also particularly preferred in combination with R$_1$ is equal to lower alkyl and more particularly where R$_1$ is methyl.

Where A is

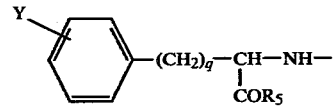

in either Formula Ia or Ib, preferred substituents are, independently, q is 2; Y is hydrogen; R$_5$ is hydrogen or methoxy or ethoxy. Particularly preferred are such A substituents where q is 2, R$_5$ is ethoxy and Y is hydrogen. The latter combination is particularly preferred in combination with R$_1$ of Formula Ia or Ib equal to lower alkyl and more particularly where R$_1$ is methyl.

Where A is

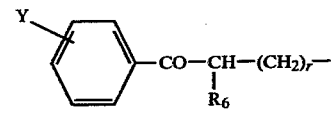

in either Formula Ia or Ib, preferred substituents are, independently, r is 0; Y is hydrogen; and R$_6$ is thiol. Particularly preferred are such substituents where r is 0; Y is hydrogen and R$_6$ is thiol. The latter combination is particularly preferred in combination with R$_1$ of Formula Ia or Ib equal to lower alkyl and more particularly where R$_1$ is methyl.

The following are preferred (lower alkyl) sulfonylamides of the invention:

2,3-dihydro-1-(3-mercapto-2-methyl-1-oxopropyl)-N-alkylsulfonyl-1H-indole-2-carboxamide;

1-[2-[[1-(ethoxycarbonyl)-3-phenylpropyl]amino]-1-oxopropyl]-2,3-dihydro-N-alkylsulfonyl-1H-indole-2-carboxamide;

1-(3-mercapto-2-methyl-1-oxopropyl)-N-alkylsulfonyl-2-pyrrolidinecarboxamide;

3-(3-mercapto-2-methylpropanoyl)-N-alkylsulfonyl-thiazolidine-4-carboxamide;

N-(1-ethoxycarbonyl-3-phenylpropyl)-alanyl-N-alkyl-sulfonyl-prolineamide;

1-(3-acetylthio-3-benzoyl-2-methylpropionyl)-N-alkyl-sulfonylprolineamide;

1-(3-mercapto-2-methylpropanoyl)-5-phenyl-N-alkyl-sulfonyl-prolineamide; and 1-(3-benzoyl-3-mercapto-2-methylpropanoyl)-N-alkyl-sulfonyl-prolineamide.

Particularly preferred are the methyl-sulfonyl derivatives of these compounds.

The compounds of Formula Ia and Ib have one or more assymetric centers and can therefore be optically active. In naming particular compounds, the direction of the optical rotation may be designated by the "+, —" convention or by the "d, l" convention. Similarly, the absolute configuration may be designated by the "D, L" convention or by the "R, S" convention. Such conventions and their use are well-known in the art. Such stereoisomers or mixtures of stereoisomers, including racemic mixtures, of the compounds of Formulas Ia and Ib are also within the scope of the invention. Generally, the preferred pyrrolidines and indolines of the invention have the S configuration at the chiral center to which the alkylsulfonylaminocarbonyl group is attached. Due to the nature of the RS convention, the preferred thiazolidines of the invention have the R configuration at this chiral center instead of the S configuration. Further, the chiral center to which the $R_1$ group is attached is preferably in the S configuration.

Additionally, where $R_7$ and $R_8$ are different, such compounds of Formula Ia may be designated as cis or trans isomers with regard to the relative positions of the $R_7$ or $R_8$ moiety and the methylsulfonylaminocarbonyl moiety. Such epimers or mixtures thereof are also within the scope of the invention.

The following are the preferred stereoisomers of the (lower alkyl)sulfonyl amides listed above:
(L)-(2S)-2,3-dihydro-1-((2S)-3-mercapto-2-methyl-1-oxopropyl)-N-alkylsulfonyl-1H-indole-2-carboxamide;
(−)-(S)-1-[(2S)-2-[[(1S)-1-(ethoxycarbonyl)-3-phenylpropyl]amino]-1-oxopropyl]-N-alkylsulfonyl-1H-indole-2-carboxamide;
(S)-1-[(2S)-3-mercapto-2-methyl-1-oxopropyl]-N-alkylsulfonyl-2-pyrrolidinecarboxamide;
(S)-3-[(2S)-3-mercapto-2-methylpropanoyl]-N-alkylsulfonyl-thiazolidine-4-carboxamide;
N-(1-ethoxycarbonyl-3-phenylpropyl)-L-alanyl-N-alkylsulfonyl-L-prolineamide;
(S)-1-[(2S)-3-acetylthio-3-benzoyl-2-methylpropanoyl]-N-alkylsulfonyl-pyrrolidine-2-carboxamide;
(S)-1-[(2S)-3-mercapto-2-methylpropanoyl]-5-phenyl-N-alkylsulfonyl-pyrrolidine-2-carboxamide; and
(S)-1-[(2S)-3-benzoyl-3-mercapto-2-methylpropanoyl]-N-alkylsulfonyl-pyrrolidine-2-carboxamide.
Particularly preferred are the methylsulfonyl derivatives of these compounds.

The (lower alkyl)sulfonyl amides of Formulas Ia and Ib are made by reacting the corresponding carboxylic acid with the desired (lower alkyl)sulfonylisocyanate. Such reactions are known in the art and, for example, are described by G. Lohaus in Chemische Berichte, 100, 2719–2729 (1967) (chlorsulfonylisocyanates with carboxylic acids) and in Belgium Brevet D'Invention No. 856,326, published Dec. 30, 1977 (Schering, AG). In carrying out such reactions, it may be necessary to first protect other possible reactant groups on the carboxylic acid reactant group. For example, if the desired compound of Formula Ia or Ib has a terminal mercapto group on the nitrogen side-chain (i.e. where A is HS—$(CHR_3)_p$—), the benzoylthio precursor would be reacted with the isocyanate before removing the protective benzoyl group. Such protection and deprotection methods are well-known in the art.

The preparation of carboxylic acid starting materials is described in references a–l listed above, as well as in other references. The (lower alkyl)sulfonylisocyanates may be made by first forming the desired (lower alkyl)sulfonylurethane [also called (lower alkyl)sulfonylcarbamates] and then heating the resulting urethane under dealkoxylation conditions, preferably using $P_2O_5$ as the reduction catalyst. The first step is described by Cassady et al., Journal of Organic Chemistry, 23, 923 (1958). The dealkoxylation step is described in U.S. Pat. No. 3,185,677, issued May 25, 1965, to Horace R. Davis.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salts, N-methyl-D-glucamine, salts with amino acids like arginine, lysine, and the like. Also salts with organic and inorganic acids may be prepared, e.g. HCl, HBr, $H_2SO_4$, $H_3RO_4$, methanesulfonic, toluenesulfonic, maleic, fumaric, camphorsulfonic. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The angiotensin converting enzyme (ACE) inhibitory property of the compounds is measured in vitro and in vivo. The in vitro assay utilizes rabbit lung extract and a specific tripeptide substrate, hippuryl-L-histidyl-L-leucine being preferred, and follows the method of Cushman et al., Biochem. Pharmacol, 20, 1637–1648 (1971).

When measured according to this procedure, the compounds of Examples 1 and 2 showed 35–38% inhibition of angiotensin converting enzyme at concentrations of 100 ng/ml. and 80% inhibition of angiotensin converting enzyme at concentrations of 1000 ng/ml. The compound of Example 3, 14–21% inhibition at concentrations of 50 ng/ml., 31–37% inhibition at 100 ng/ml., and 76–80% inhibition at concentrations of 1000 ng/ml. The compound of Example 4 showed 32% inhibition at 50 ng/ml., 50–57% inhibition at 50 ng/ml. and 89–92% inhibition of angiotensin converting enzyme at 1000 ng/ml.

The in vivo ACE inhibitory activity of the compounds is measured according to the procedure described in Rubin et al., J. Pharmacol. Exp. Ther., 204, 271–280 (1978), which utilizes the conscious normotensive rat as a subject. In this procedure, the jugular vein and carotid artery cannulae are placed in an ether-anesthetized, normotensive, male, Sprague-Dawley rat for injection or oral dosage of compounds and direct recording of systemic arterial pressure, respectively. The blood pressure responses to I.V. injections of angiotensin I (300 ng/kg.), angiotensin II (100 ng/kg.) and bradykinin (10 μg/kg.) are recorded and compared with identical doses administered at various time intervals after oral dosing of a prospective angiotensin converting enzyme inhibitor. An angiotensin converting enzyme inhibitor would not be expected necessarily to lower arterial pressure in the normotensive rat, but would be expected to block angiotensin I pressor responses without grossly altering angiotensin II responses. Additionally, the vasodepressor response to bradykinin would be expected to be augmented since angiotensin converting enzyme is known to inactivate bradykinin normally.

The anti-hypertensive effect of the compounds of the invention is measured in the spontaneously hypertensive rat. In this procedure systolic pressure of male spontaneously hypertensive rats is measured by an indirect technique using the Decker Caudal Plethysmograph or other appropriate sensor. Groups usually consist of four or more rats. Drugs are usually administered orally. Pressures are usually read prior to drug administration and at 1.5, 4 and 24 hours thereafter. This schedule may be altered depending upon the behavior of the drug.

This procedure measures the hypotensive effect of the subject compounds in a hypertensive subject using a single dose and measuring the response over a 24 hour period. When used to treat hypertension in warm-blooded animals, including humans, doses of less than 50 mg/kg/day are preferred and doses of less than 10 mg/kg/day are desired. Such effective treatment doses would generally be administered in long-term antihypertensive therapy. Angiotensin converting enzyme inhibitors when utilized as anti-hypertensive agents are most effective upon such extended administration and exhibit no significant side-effects when administered at moderate or low doses. As noted earlier, the compounds of the invention exhibit a hypotensive (depressor) response only when administered to hypertensive subjects and would not be expected to lower blood pressures significantly in normotensive subjects.

The compounds of Formulas Ia and Ib (and the disulfides thereof) may be administered orally, intravenously, intraperitoneally, intramuscularly, or subcutaneously. Oral administration is preferred. Further, the compounds of the invention may be administered in combination with other antihypertensive agents and/or with diuretic agents in an overall therapeutic program for a particular patient. In such cases the dose of the compound of the invention would normally be less than utilized if the compound alone were utilized in the antihypertensive therapy.

When employed to lower blood pressures in hypertensive subjects, the effective dosage of the compound being utilized for such treatment will vary according to the particular compound being employed, the severity and nature of condition being treated, and the particular subject being treated.

Further, when employed as anti-hypertensive agents or as angiotensin converting enzyme inhibitors, the compounds of the invention may be administered alone or in combination with pharmaceutically acceptable carriers. The proportion and nature of such carriers would be determined by the solubility and other chemical properties of the compound selected, the chosen route of administration, etc. in accordance with standard pharmaceutical practices.

This invention also includes methods of treatment of hypertension in warm-blooded animals utilizing hypotensively effective amounts of the compounds of Formulas Ia and Ib (and the disulfides thereof). The generic and subgeneric aspects of this part of the invention encompass the same compounds and groups of compounds described above with respect to the compound portion of the invention.

The invention is further illustrated by the following examples.

EXAMPLE 1

Benzenecarbothioic Acid
S-[(2S)-2-Methyl-3-[(2S)-2-[(Methylsulfonylamino)Carbonyl]-1-Pyrrolidinyl]-3-Oxopropyl]Ester,
Dicyclohexylamine Salt To a magnetically stirred solution of 1-[(2S)-3-(benzoylthio)-2-methyl-1-oxopropyl]-L-proline (2.52 g., prepared according to methods described in U.S. Pat. No. 4,105,776, M. A. Ondetti and D. W. Cushman to Squibb and Sons) in dry (3A molecular sieves) acetonitrile (20 ml.) cooled in an ice bath was added dropwise approximately 2½ ml. of a solution of methanesulfonylisocyanate (1 ml., d=1.412) prepared according to U.S. Pat. No. 3,185,677, H. R. Davis to 3M Co. in dry acetonitrile (5 ml.), followed by N,N-diisopropylethylamine (1.36 ml., d=0.742). The remainder of the methanesulfonylisocyanate solution (ca. 2½ ml.) was then added. Ten minutes later an additional 0.5 ml. of neat methanesulfonylisocyanate was added directly to the solution. The cooling bath was removed and the reaction solution, protected from moisture, was stirred at room temperature for 2 hours. The solution was evaporated to a syrup which was treated with ice and dichloromethane. The mixture was acidified to ph 1 by the addition of potassium bisulfate solution and the mixture was shaken. The organic layer was separated and the aqueous phase was extracted several more times with dichloromethane. The combined organic extracts were washed twice with saturated brine and dried (MgSO4). Evaporation gave a syrup which after drying under oil pump vacuum gave 3.57 g. of crude, syrupy product. TLC on silicAR 7GF (Mallinckrodt) with ethyl acetate as developer revealed two components which had different Rf values from starting material. An initial attempt to separate the two components on a column (38×3.1 cm.) of silica gel (J. T. Baker) prepacked in chloroform failed. The chloroform eluate containing both components was evaporated to a syrup which was dried under oil pump vacuum. The residual syrup (2.49 g.) was submitted to an HPLC separation on a silica gel, "Prep Pak" (Water Associates) column. Elution with ethyl acetate-hexane (1:1) removed the major faster moving component. Elution with ethyl acetate removed the second slow-moving component. The HPLC separation was also readily monitored by the TLC with the above mentioned system and appropriate fractions were concentrated to give the fast-moving component as a yellow syrup (1.06 g., 40% of syrupy purified titled compound as the free acid). The slower component was isolated as a white opaque foam (0.65 g.).

The major component was dissolved in a small volume of ethyl acetate and N,N-dicyclohexylamine was added in slight excess. Crystals of slightly impure titled compound formed quickly. Addition of heptane completed the crystallization; yield 1.20 g. (78% yield for salt formation), m.p.=164°–167°. The product was dissolved in methanol and the solution was decolorized. Evaporation gave a syrup which was crystallized from ethyl acetate-heptane; yield=0.75 g. (16% from 1-[(2S)-3-(benzoylthio)-2-methyl-1-oxopropyl]-L-proline], m.p.=168°–170°, $[\alpha]_D^{25.5}= -70.72°$ (c=1.03, EtOH), M+ 398 (E.I.), $\lambda_{max}^{KBr}$ 3440, 1660, 1610 cm$^{-1}$, pmr (CDCl3) δ1.30 (d, $J_{Me,H}$6 Hz, propyl chain Me), 3.06 (s, MeSO2—), 4.24–4.44 (m, rough triplet, H at 2-position of proline ring), 7.30–7.80 (m, φCO), 7.83–8.08 (m, φCO).

Analysis for: $C_{17}H_{22}N_2O_5S_2\cdot C_{12}H_{23}N$: Calculated: C, 60.07; H, 7.82; N, 7.25: Found: C, 60.24; H, 7.83; N, 7.50.

The structure of the slow moving component was not determined. It had the following elemental analysis: C, 45.06; H, 5.25; N, 8.43 and M+ 513 (E.I.).

EXAMPLE 2

Benzenecarbothioic Acid S-[(2S)-2-Methyl-3-[(2S)-2-[(Methylsulfonylamino)Carbonyl]-1-Pyrrolidinyl]-3-Oxopropyl]Ester, Dicyclohexylamine Salt To a magnetically stirred solution of 1-[(2S)-3-(benzoylthio)-2-methyl-1-oxopropyl]-L-proline (10.78 g., prepared according to methods described in U.S. Pat. No. 4,105,776, M. A. Ondetti and D. W. Cushman to Squibb and Sons) in dry (3 A molecular sieves) acetonitrile (100 ml.) under a nitrogen atmosphere was added N,N-diisopropylethylamine (5.84 ml., d=0.742) and the solution was cooled in an ice bath. Methanesulfonylisocyanate (3.45 ml., d=1.412, prepared according to U.S. Pat. No. 3,185,677, H. R. Davis to 3M Company) in dry acetonitrile (10 ml.) was then added dropwise from a funnel over the course of 12 minutes. The dropping funnel was rinsed with a further 5 ml. of acetonitrile to complete the addition. The ice bath was removed and the solution was stirred under nitrogen at room temperature for 4½ hours. After that time, bubbling had ceased and the resulting yellow solution was evaporated to a syrup. The syrup was treated with ice and dichloromethane and the mixture was acidified to pH 1 by the addition of potassium bisulfate solution. After thorough mixing the organic layer was separated and the aqueous phase was extracted four more times with dichloromethane. The combined organic extracts were washed twice with saturated brine and dried ($MgSO_4$). Evaporation gave a syrup which after drying under oil pump vacuum gave 13.89 g. of crude product. To a stirred solution of that material in ethyl acetate (70 ml.) was added N,N-dicyclohexylamine dropwise in slight excess. Crude titled compound crystallized readily. Addition of heptane and cooling in ice completed crystallization; yield=18.61 g. (96%), m.p. 167°–170°. The white crystals were dissolved in methanol and the solution was evaporated to smaller volume. The solution was coevaporated with ethyl acetate and the titled compound was crystallized from ethyl acetate-heptane; yield=15.70 g. (81%), m.p. 170°–172°, $[\alpha]_D^{25} = -71.48°$ (c=0.995, EtOH), $\lambda_{max}^{KBr}$ 3440, 1660, 1610 cm$^{-1}$, pmr (CDCl$_3$) δ1.30 (d, $J_{Me,H}$6 Hz, propyl chain Me), 3.06 (s, MeSO$_2$—), 4.24–4.44 (m, rough triplet, H at 2-position of proline ring), 7.30–7.80 (m, φCO), 7.83–8.08 (m, φCO).

Analysis for: $C_{17}H_{22}N_2O_5S_2\cdot C_{12}H_{23}N$: Calculated: C, 60.07; H, 7.82; N, 7.25; Found: C, 60.11; H, 7.61; N, 7.19.

EXAMPLE 3

Benzenecarbothioic Acid S-[(2S)-2-Methyl-3-[(2S)-2-[(Methylsulfonylamino)Carbonyl]-1-Pyrrolidinyl]-3-Oxopropyl]Ester Benzenecarbothioic acid S-[(2S)-2-methyl-3-[(2S)-2-methyl-3-[(2S)-2-(methylsulfonylamino)carbonyl]-1-pyrrolidinyl]-3-oxopropyl]ester dicyclohexylamine salt (2.00 g.) was mixed with ethyl acetate and an excess of an aqueous solution of potassium bisulfate. The aqueous layer was extracted a further two times and the combined organic extracts were washed with saturated brine and dried (MgSO$_4$). The solution was treated with charcoal and filtered through celite. Evaporation gave a foam which was dried under oil pump vacuum; yield=1.37 g. (100%); MH+ 399 (C.I.), $[\alpha]_D^{25} = -190.12°$ (c=1.665, chloroform), $\lambda_{max}^{KBr}$3420, 1715(—CONH—), 1660, 1620, 1340(SO$_2$), 1130(SO$_2$), 700(φ-)cm$^{-1}$; pmr(CDCl$_3$), δ1.33 (d, $J_{Me,H}$, 6 Hz, propyl chain Me), 3.25 (s, MeSO$_2$), 4.50–4.75 (m, H at 2-position of proline ring), 7.30–7.75 (m, φCO—), 7.80–8.06 (m, φCO—).

Analysis for: $C_{17}H_{22}N_2O_5S_2$: Calculated: C, 51.24; H, 5.56; N, 7.03; Found: C, 50.66; H, 5.58; N, 6.75.

EXAMPLE 4

(S)-1-[(2S)-3-Mercapto-2-Methyl-1-Oxopropyl]-N-(Methylsulfonyl)-2-Pyrrolidinecarboxamide Benzenecarbothioic acid S-[(2S)-2-methyl-3-[(2S)-2-[(methylsulfonylamino)carbonyl]-1-pyrrolidinyl]-3-oxopropyl]ester, dicyclohexylamine salt, from Example 2 (10.00 g.) was converted into the free acid as described above, and the resulting foam (7.10 g.) was dissolved in 2-methoxyethylamine (75 ml.) and the solution was kept under nitrogen at room temperature for one hour. The excess reagent was removed by evaporation and the resulting syrup was dissolved in water. The aqueous solution was extracted (×4) with ethyl acetate to remove 2-methoxyethylbenzamide. The aqueous solution was acidified with aqueous potassium bisulfate to pH 1 and extracted (×4) with ethyl acetate. The combined organic extracts were washed with saturated brine and dried (MgSO$_4$). Evaporation gave a syrup which was subjected to an oil pump vacuum; yield: 4.65 g. (92%), MH+ 295(C.I.), $[\alpha]_D^{25} = -109.77°$ (c=1.09, ethanol), $\lambda_{max}^{film}$ 3080, 2570(SH), 1715(—CONH—), 1610 (—CON<), 1330(SO$_2$), 1130(SO$_2$) cm$^{-1}$, δ1.21 (d, $J_{Me,H}$6 Hz, propyl chain Me), 1.50 (rough triplet, width 16 Hz, "J"8 Hz, SH), 3.27 (s, MeSO$_2$—), 4.52–4.83 (m, H at 2-position of proline ring).

Analysis for: $C_{10}H_{18}N_2O_4S_2$: Calculated: C, 40.80; H, 6.16; N, 9.52; Found: C, 41.30; H, 6.12; N, 8.77.

What is claimed is:

1. A compound of the formula:

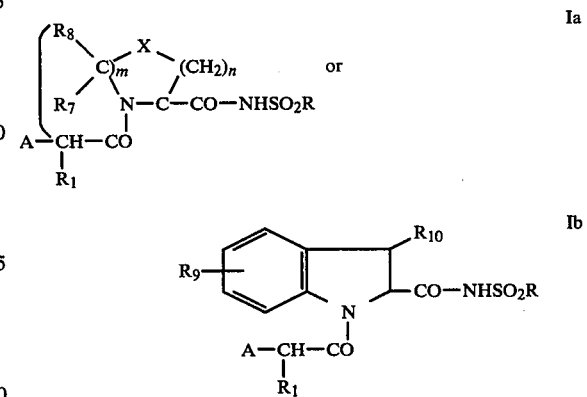

wherein:
   m is 0 or 1, and m is 1 when X is S;
   n is 1 or 2;
   X is —CH$_2$— or S;
   R is methyl, ethyl, n-propyl, or iso-propyl;
   R$_7$ is hydrogen, lower alkyl, lower alkoxy, phenyl, or substituted phenyl;

$R_8$ is hydrogen or lower alkyl;

$R_9$ is hydrogen, hydroxy, lower alkyl, lower alkoxy, or halogen;

$R_{10}$ is hydrogen or lower alkyl;

$R_1$ is hydrogen, lower alkyl, phenyl, substituted phenyl, phen-lower alkyl, substituted phen lower alkyl, amino lower alkyl, or perfluoroalkyl;

A is:

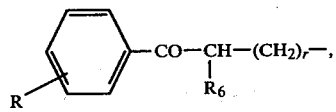

in which:

$R_2$ is hydrogen or $R_4CO-$ where $R_4$ is hydrogen, lower alkyl, phenyl, substituted phenyl, phen lower alkyl, or substituted phen lower alkyl;

$R_3$ is hydrogen, lower alkyl, benzoyl, or substituted benzoyl;

$R_6$ is $SR_{11}$ where $R_{11}$ is hydrogen, lower alkanoyl, benzoyl, substituted benzoyl, benzoxycarbonyl, or substituted benzoxycarbonyl;

$R_5$ is hydroxy, lower alkoxy or amino;

Y is hydrogen, halogen, a lower alkyl group, or a lower alkoxy group;

p is 0 or 1;

q is 0–3; and r is 0 or 1.

2. A compound of claim 1 wherein A is $R_2-S-(CHR_3)_p-$.

3. A compound of claim 2 wherein p is 1.

4. A compound of claim 2 wherein $R_3$ is hydrogen or benzoyl.

5. A compound of claim 2 wherein $R_2$ is hydrogen, benzoyl or acetyl.

6. A compound of claim 2 wherein $R_1$ is lower alkyl.

7. A compound of claim 2 wherein p is 1, $R_2$ and $R_3$ are hydrogen, and $R_1$ is methyl.

8. A compound of claim 7 in which the alkylsulfonylamide carbonyl group and the $R_1$ methyl group are attached to the only two assymetric carbon atoms and which is the S,S stereoisomer thereof.

9. A compound of claim 1 wherein A is:

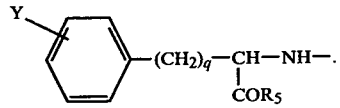

10. A compound of claim 9 wherein q is 2.

11. A compound of claim 9 wherein Y is hydrogen.

12. A compound of claim 9 wherein $R_5$ is hydrogen, methoxy or ethoxy.

13. A compound of claim 9 wherein q is 2, $R_5$ is ethoxy, Y is hydrogen, and $R_1$ is methyl.

14. A compound of claim 13 having only three assymetric carbon atoms to which are attached, respectively, the alkylsulfonylamide carbonyl group, the $R_1$ methyl group and the $COR_5$ ethoxy-carbonyl group, which is the S,S,S stereoisomer thereof.

15. A compound of claim 1 wherein A is:

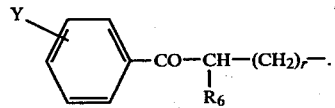

16. A compound of claim 15 wherein r is 0.

17. A compound of claim 15 wherein Y is hydrogen.

18. A compound of claim 15 wherein $R_6$ is thiol.

19. A compound of claim 15 wherein r is 0; Y is hydrogen; $R_6$ is thiol; and $R_1$ is methyl.

20. A compound of claim 19 having two assymetric carbon atoms to which are attached the alkylsulfonylamide carbonyl group and the $R_1$ methyl group, which are in the S stereoisomeric configuration, and having a third assymetric carbon atom to which is attached the $R_6$ thiol group, which is the S or R stereoisomer thereof.

21. A compound of claim 1 selected from a group consisting of:

2,3-dihydro-1-(3-mercapto-2-methyl-1-oxopropyl)-N-alkylsulfonyl-1H-indole-2-carboxamide;

1-[2-[[1-(ethoxycarbonyl)-3-phenylpropyl]-amino]-1-oxopropyl]-2,3-dihydro-N-alkylsulfonyl-1H-indole-2-carboxamide;

1-(3-mercapto-2-methyl-1-oxopropyl)-N-alkylsulfonyl-2-pyrrolidinecarboxamide;

3-(3-mercapto-2-methylpropanoyl)-N-alkylsulfonyl-thiazolidine-4-carboxamide;

N-(1-ethoxycarbonyl-3-phenylpropyl)-alanyl-N-alkylsulfonyl-prolineamide;

1-(3-acetylthio-3-benzoyl-2-methylpropionyl)-N-alkylsulfonylprolineamide;

1-(3-mercapto-2-methylpropanoyl)-5-phenyl-N-alkylsulfonyl-prolineamide; and 1-(3-benzoyl-3-mercapto-2-methylpropanoyl)-N-alkylsulfonyl-prolineamide.

22. A compound of claim 21 which is the N-methylsulfonyl derivative thereof.

23. A stereoisomer of a compound of claim 1 selected from a group consisting of:

(1)-(2S)-2,3-dihydro-1-((2S)-3-mercapto-2-methyl-1-oxopropyl)-N-alkylsulfonyl-1H-indole-2-carboxamide;

(−)-(S)-1-[(2S)-2-[[(1S)-1-(ethoxycarbonyl)-3-phenylpropyl]amino]-1-oxopropyl]-N-alkylsulfonyl-1H-indole-2-carboxamide;

(S)-1-[(2S)-3-mercapto-2-methyl-1-oxopropyl]-N-alkylsulfonyl-2-pyrrolidinecarboxamide;

(S)-3-[(2S)-3-mercapto-2-methylpropanoyl]-N-alkylsulfonyl-thiazolidine-4-carboxamide;

N-(1-ethoxycarbonyl-3-phenylpropyl)-L-alanyl-N-alkylsulfonyl-L-prolineamide;

(S)-1-[(2S)-3-acetylthio-3-benzoyl-2-methylpropanoyl]-N-alkylsulfonyl-pyrrolidine-2-carboxamide;

(S)-1-[(2S)-3-mercapto-2-methylpropanoyl]-5-phenyl-N-alkylsulfonyl-pyrrolidine-2-carboxamide; and (S)-1-[(2S)-3-benzoyl-3-mercapto-2-methylpropanoyl]-N-alkylsulfonyl-pyrrolidine-2-carboxamide.

* * * * *